US007673631B2

(12) United States Patent
Astani et al.

(10) Patent No.: US 7,673,631 B2
(45) Date of Patent: *Mar. 9, 2010

(54) ADJUSTABLE VAGINAL SPLINT FOR PELVIC FLOOR SUPPORT

(75) Inventors: Aida Astani, Hamburg (DE); Burkhard Peters, Wattenbeck (DE); Marcus P. Carey, Eltham (AU)

(73) Assignee: Ethicon, Inc., Somerville, NJ (US)

( * ) Notice: Subject to any disclaimer, the term of this patent is extended or adjusted under 35 U.S.C. 154(b) by 498 days.

This patent is subject to a terminal disclaimer.

(21) Appl. No.: 11/334,966

(22) Filed: Jan. 19, 2006

(65) Prior Publication Data

US 2007/0089750 A1    Apr. 26, 2007

Related U.S. Application Data

(63) Continuation-in-part of application No. 11/258,441, filed on Oct. 25, 2005.

(51) Int. Cl.
*A61F 6/06* (2006.01)
(52) U.S. Cl. ............... 128/834; 128/836; 128/DIG. 25; 600/29
(58) Field of Classification Search ................ 128/885, 128/830, 834, 836, DIG. 25; 600/37, 29; 215/319; 220/23.89, 287; 119/863, 865; 446/4
See application file for complete search history.

(56) References Cited

U.S. PATENT DOCUMENTS

| | | | |
|---|---|---|---|
| 2,475,071 A | | 7/1949 | Young |
| 5,228,570 A | * | 7/1993 | Robinson ............... 206/378 |
| 5,259,278 A | * | 11/1993 | Leas ..................... 81/180.1 |
| 5,297,687 A | * | 3/1994 | Freed ..................... 215/206 |

(Continued)

FOREIGN PATENT DOCUMENTS

CA    331100 A    3/1933

(Continued)

OTHER PUBLICATIONS

Samuelsson, E. C. et al. "Signs of genital prolapse in a Swedish population of women 20 to 59 years of age and possible related factors", Am. J. Obstet Gynecol. 180:299-305 (1999).

(Continued)

*Primary Examiner*—Patricia Bianco
*Assistant Examiner*—Camtu T Nguyen

(57) ABSTRACT

Vaginal splint assemblies and methods for their use for treating various pelvic floor conditions are provided. One embodiment of a vaginal splint assembly includes a base portion having a connecting portion and first and second sides extending outwardly from first and seconds ends of the connecting portion to first and second free ends respectively. It further includes a plurality of apical sections each of a different size and each having a connecting portion and first and second sides extending outwardly from first and second ends of the connecting portion to first and second free ends respectively, and at least first and second coupling elements. The first coupling element is capable of securing the first free end of the base portion to the first free end of any one of the plurality of apical sections, and the second coupling element is capable of securing the second free end of the base portion to the second free end of the one apical section.

18 Claims, 7 Drawing Sheets

U.S. PATENT DOCUMENTS

| | | | |
|---|---|---|---|
| 5,509,332 A * | 4/1996 | Donaldson, Jr. ............... 81/59.1 |
| 6,131,576 A | 10/2000 | Davis | |
| 6,216,353 B1 | 4/2001 | Schenck | |
| 6,216,698 B1 | 4/2001 | Regula | |
| 6,543,141 B1 | 4/2003 | Biehl | |
| 6,905,472 B2 * | 6/2005 | Welch ......................... 600/591 |
| 7,036,511 B2 * | 5/2006 | Nissenkorn ................. 128/834 |
| 2005/0016545 A1 | 1/2005 | Nissenkorn | |
| 2007/0088189 A1 | 4/2007 | Levy | |

FOREIGN PATENT DOCUMENTS

| | | |
|---|---|---|
| CA | 600904 A | 7/1960 |
| DE | 37 20 858 A | 1/1989 |
| DE | 9104155 U1 | 6/1991 |
| EP | 0084755 A | 8/1983 |
| RU | 961061 | 3/1999 |
| RU | 2196519 C2 | 1/2003 |
| RU | 2232562 C2 | 7/2004 |
| WO | WO 96/01084 A1 | 1/1996 |
| WO | WO 2004/045457 A1 | 6/2004 |

OTHER PUBLICATIONS

Olsen, A. L. et al. "Epidemiology of Surgically Managed Pelvic Organ Prolapse and Urinary Incontinence", Obstet Gynecol vol. 89, No. 4, 501-506 (1997).

Winters, J. C. et al. "Abdominal Sacral Colpopexy and Abdominal Enterocele Repair in the Management of Vaginal Vault Prolapse", Urology 55-63 (2000).

Deval, B. et al., What's new in prolapse surgery? Current Opinion in Urology 13:315-323 (2003).

Maher, C.F. et al., "Abdominal sacral colpopexy or vaginal sacrospinous colpopexy for vaginal vault prolapse: A prospective randomizer study", Am. J. Obstet Gynecol 190:20-26 (2004).

Cervigni, M., et al., "The use of synthetics in the treatment of pelvic organ prolapse. Current Opinion in Urology" 11:429-435 (2001).

Visco, A. C., et al., "Vaginal mesh erosion after abdominal sacral colpopexy", Am. J. Obstet Gynecol 184:297-302 (2001).

Boyles, S.H. et al., "Procedures for pelvic organ prolapse in the United States 1979-1997", American Journal of Obstetric Gynecology 188: 108-115(2003).

Pang, Man-Wah, et al., "An overview of pelvic floor reconstructive surgery for pelvic organ prolapse", Journal of Paediatrics, Obstetrics and Gynaecology. (2003).

Kulakov, V.I. et al., Operative Gynecology, A Manual for Physicians, pp. 206-207, The NGMA Publishing House (1998).

* cited by examiner

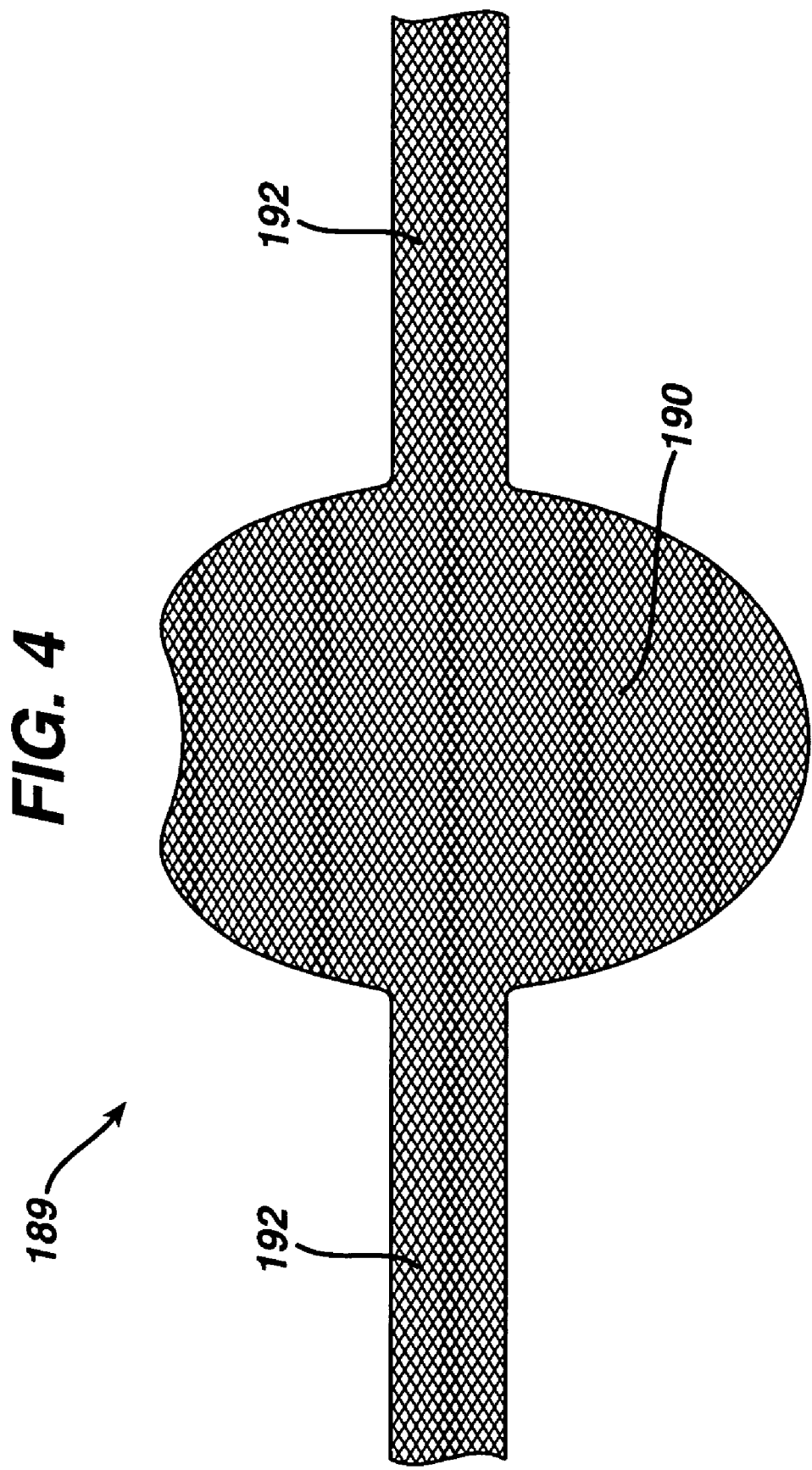

ADJUSTABLE VAGINAL SPLINT FOR PELVIC FLOOR SUPPORT

CROSS-REFERENCE TO RELATED APPLICATIONS

The present application is a continuation-in-part of U.S. patent application Ser. No. 11/258,441, filed on Oct. 25, 2005.

BACKGROUND OF THE INVENTION

1. Field of the Invention

The present invention relates to devices suitable for use in repairing various pelvic floor prolapse conditions. More particularly, the present invention relates to vaginal implants for such uses.

2. Background Discussion

Each year in the USA approximately 200,000 women undergo pelvic organ prolapse surgery. Pelvic organ prolapse generally involves the descent of one or more of the uterus, the bladder or the rectum along the vagina towards (or in extreme cases protruding beyond) the introitus. Women of advancing years, or those that have borne several children are more frequent sufferers of pelvic organ prolapse. Traditional vaginal surgery to address these conditions is associated with a high failure rate of between 30-40%. Complex and elaborate abdominal, vaginal and laparoscopic procedures such as abdominal sacral colpopexy, transvaginal sacrospinous ligament fixation, and laparoscopic sacral colpopexy have been developed to reduce the risk of prolapse recurrence. Unfortunately these procedures require a high level of surgical expertise and are only available to a small number of specialist practitioners and therefore to a small number of patients. Details of various procedures currently in use are described in Boyles S H., Weber A M, Meyn L. "Procedures for pelvic organ prolapse in the United States", 1979-1997, American Journal of Obstetric Gynecology 2003, 188; 108-115.

Recently there has been a trend towards the use of reinforcing materials to support a vaginal wall damaged by prolapse. Prosthetic materials such as donor fascia lata, pig dermis and various types of synthetic mesh have been utilized with mixed success. These materials are generally positioned under the vaginal wall or walls and sutured into position.

WO 2004/045457 discloses a different approach that utilizes a prosthetic material in repairing damaged vaginal walls, and subsequently inserts an intra-vaginal splint. The splint is placed into the vagina, and operates to reduce the mobility of the vaginal walls. The repairs are typically made by dissecting either the posterior wall of the vagina, the anterior wall of the vagina, or both. A graft of either synthetic material, such as a polypropylene mesh or other fabric, or autologous or analogous material is placed in the dissected area between the vaginal wall and the prolapsing organ. The vaginal incision is then closed by suture or other tissue closure means, at which time the vaginal splint is inserted into the vagina and affixed to either wall. The splint stabilizes the vagina, keeps it elongated, and helps to hold the graft in place by preventing it from sliding or dislodging. Eventually the fascial tissue on each side of the graft will infiltrate into it thereby incorporating it into the body.

An aspect not addressed by WO 2004/045457, however, is the fact that different sized patients will require different sized splints. Simply providing the splints in numerous different sizes is not an economical solution. Co-pending U.S. patent application Ser. No. 11/258,441, which is incorporated herein by reference in its entirety, addresses this problem and provides improved implants having adjustability features, as does the present application.

SUMMARY OF THE INVENTION

The present invention provides a vaginal splint assembly including a base portion having a connecting portion and first and second sides extending outwardly from first and seconds ends of the connecting portion to first and second free ends respectively, and a plurality of apical sections. Each of the plurality of apical section are of a different size, and each have a connecting portion and first and second sides extending outwardly from first and second ends of the connecting portion to first and second free ends respectively. The assembly further includes at least first and second coupling elements, with the first coupling element being capable of securing the first free end of the base portion to the first free end of any one of the plurality of apical sections, and the second coupling element being capable of securing the second free end of the base portion to the second free end of the one apical section.

The first and second coupling elements may be coupled to, and extend outwardly from the first and second ends of the base portion to respective distal free ends. Further, the first and second free ends of each of the plurality of apical sections may have first and second recesses therein configured to receive the respective distal free ends of the first and second coupling elements. In yet another embodiment, the distal ends of the first and second coupling elements form an interference fit with the respective first and second recesses.

According to another embodiment, each of the plurality of apical sections have first and second coupling elements coupled to and extending outwardly from the first and second free ends thereof respectively. The first and second free ends of the base portion may have first and second recesses therein configured to receive the distal free ends of the first and second coupling elements of any one of the plurality of apical sections.

In yet another embodiment, for each of the plurality of apical sections, when secured to the base portion via the at least first and second coupling elements, the combination apical section and base portion has a substantially trapezoidal overall configuration.

The assembly may further include an inflatable member positioned between the first and second sides of the base portion that is inflatable by infusion of fluid or gas therein. When in the inflated state, the inflatable member extends outwardly beyond a top and/or bottom surface of the splint. The inflatable member may also be detachably coupled to the splint assembly, and may be made of polyurethane, polyester, silicone or rubber.

The disclosure also provides a method for treating a pelvic floor prolapse condition of a patient including the steps of providing a vaginal splint assembly including base portion having a connecting portion and first and second sides extending outwardly from first and seconds ends of the connecting portion to first and second free ends respectively, a plurality of apical sections each of a different size and each having a connecting portion and first and second sides extending outwardly from first and second ends of the connecting portion to first and second free ends respectively, and at least first and second coupling elements, wherein the first coupling element is capable of securing the first free end of the base portion to the first free end of any one of the plurality of apical sections, and the second coupling element is capable of securing the second free end of the base portion to the second free end of said one apical section; determining a size of the patient's vagina; based on the determined size, selecting one of the plurality of apical sections; coupling the selected apical section to the base portion via the at least first and second coupling elements to form a vaginal splint; and inserting the vaginal splint into the patient's vagina.

The first and second coupling elements may be secured to the base portion, and configured such that any one of the plurality of apical sections may be coupled to the base portion via the coupling elements. The first and second coupling elements may also extend outwardly from the first and second free ends of the base portion to respective distal ends, with the first and second free ends of each of the plurality of apical sections having respective first and second recesses therein configured to removably receive therein the respective distal free ends of the first and second coupling elements. The distal ends of the first and second coupling elements may also form an interference fit with the respective first and second recesses.

According to another method, when any one of the plurality of adjustable apical sections is secured to the base portion, the splint has a substantially trapezoidal overall configuration.

In yet another method, the splint assembly further comprises an inflatable member positioned between the first and second sides of the base portion, and the method further includes the step of, following the inserting step, inflating the inflatable member by infusing fluid or gas therein until the inflatable member extends outwardly beyond a top and/or bottom surface of the splint. The inflatable member may be a balloon comprised of a material selected from the group consisting of polyurethane, polyester, silicone and rubber.

Yet another method includes the additional step of removing the vaginal splint from the patient after a first time period has elapsed. Where the inflatable member is detachably coupled to the splint, the method may involve deflating and removing the inflatable member after a first time period has elapsed, and removing the splint after a second time period has elapsed that is greater than the first time period.

Also provided is a vaginal splint assembly including a base portion having a connecting portion and first and second sides extending outwardly from first and seconds ends of said connecting portion to first and second free ends respectively, and a plurality of apical sections each of a different size and each having a connecting portion and first and second sides extending outwardly from first and second ends of the connecting portion to first and second free ends respectively. The assembly further includes a means for coupling to the base portion, one at a time, any one of the plurality of apical sections, wherein, when so coupled, the one apical section is positioned relative to the base portion so that the first and second free ends of the base portion are substantially aligned with and opposing the first and second free ends of the one apical section. The means for coupling may further include first and second coupling elements secured to the first and second free ends of the base portion and extending outwardly therefrom to first and second distal free ends respectively, where the first and second free ends of each of the apical sections have a recess therein capable of receiving therein the first and second distal free ends of the first and second coupling elements respectively.

In yet another embodiment, for each of the plurality of apical sections, when secured to the base portion via the at least first and second coupling elements, the combination apical section and base portion has a substantially trapezoidal overall configuration.

The assembly may also further include an inflatable member positioned between the first and second sides of the base portion, the inflatable member being inflatable by infusion of fluid or gas therein, and, when in the inflated state, the inflatable member extends outwardly beyond a top and/or bottom surface of the splint. The inflatable member may be made of polyurethane, polyester, silicone or rubber.

BRIEF DESCRIPTION OF THE DRAWINGS

FIG. 4 is an exemplary mesh that can be used in conjunction with a splint for pelvic floor repair;

DETAILED DESCRIPTION OF THE INVENTION

Before explaining the present invention in detail, it should be noted that the invention is not limited in its application or use to the details of construction and arrangement of parts illustrated in the accompanying drawings and description. The invention as illustrated may be implemented or incorporated in other embodiments, variations and modifications, and may be practiced or carried out in various ways.

Figure 1:
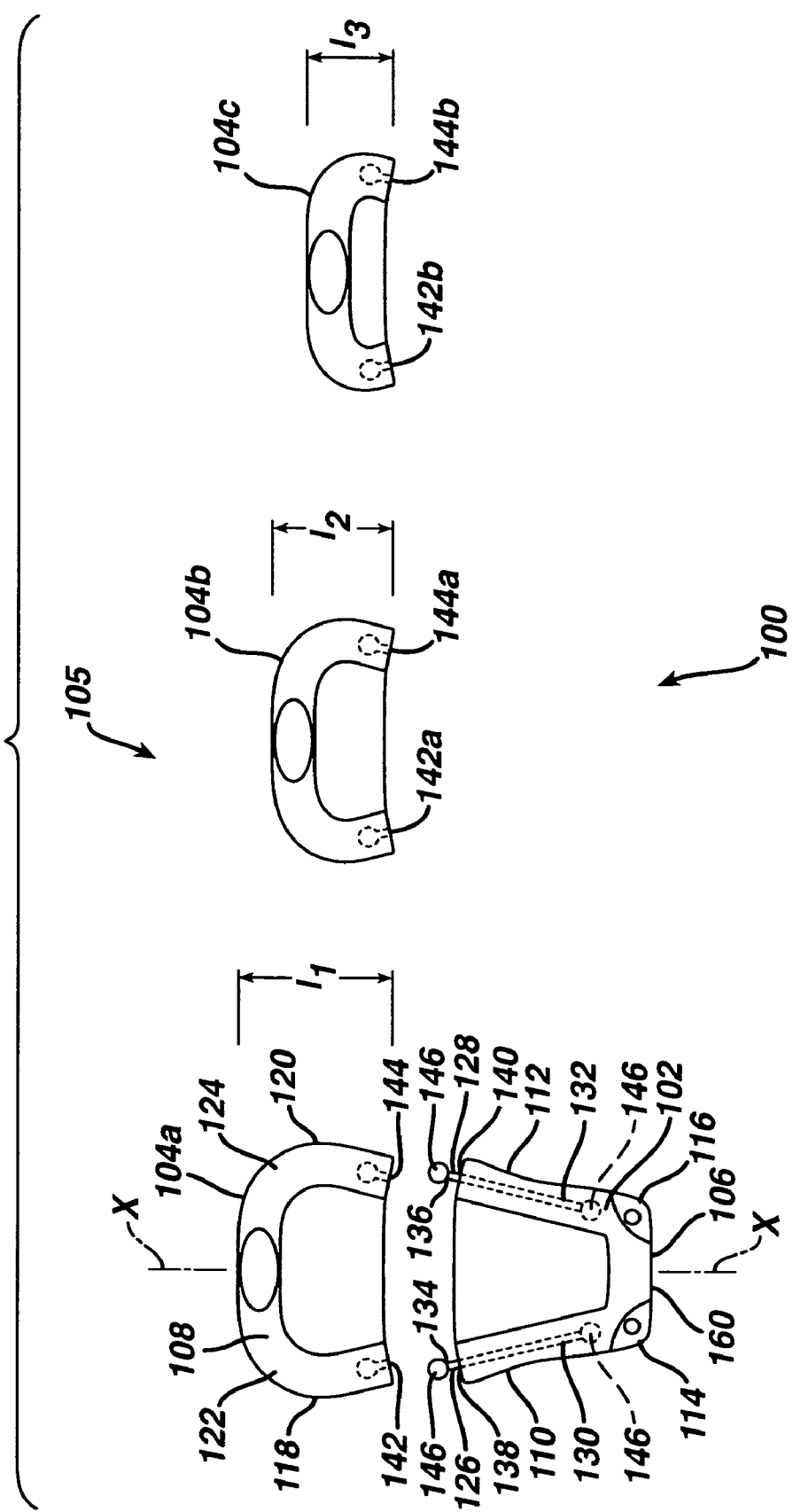
FIG. 1 is a top view illustrating one embodiment of a splint assembly according to the present invention.
Figure 2:
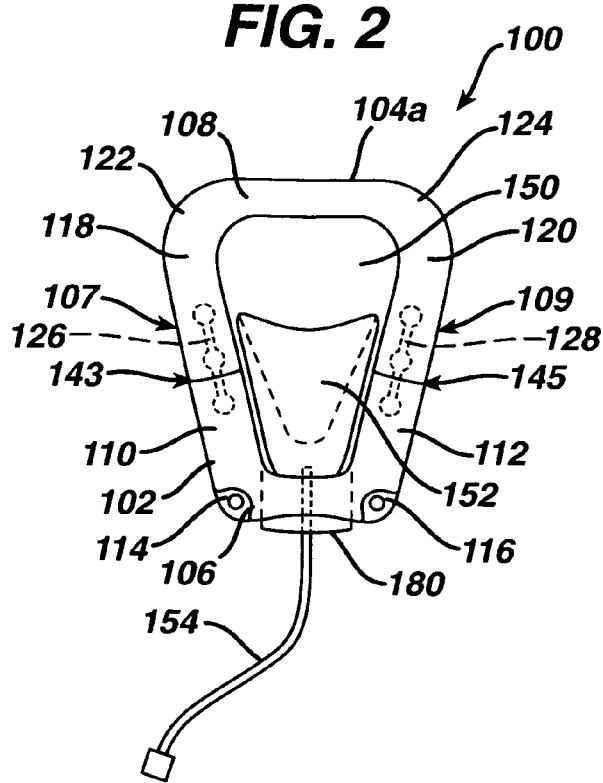
FIGS. 2, 2a and 2b are top, side and front views respectively of the embodiment of FIG. 1 having an inflatable member in a deflated state.
Figure 2A:
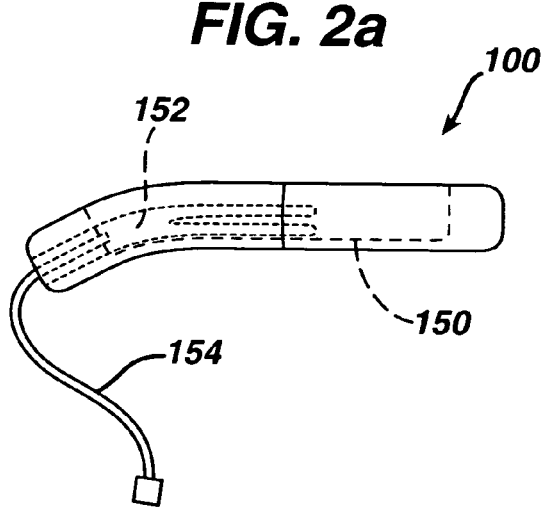
Figure 2B:
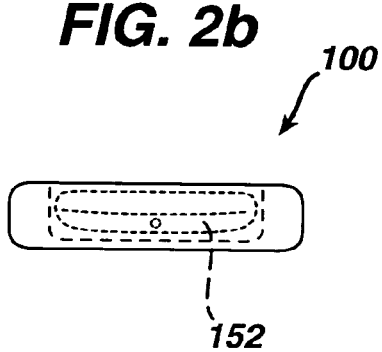
Figure 3:
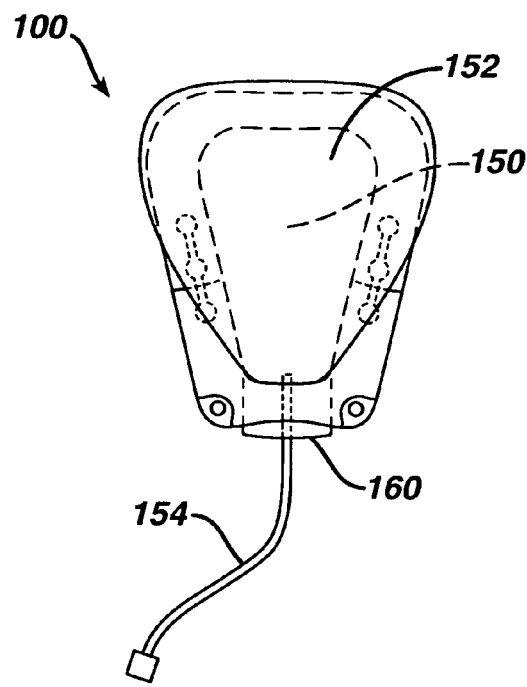
FIGS. 3, 3a and 3b are top, side and front views respectively of the embodiment of FIG. 1 with the inflatable member in an inflated state.
Figure 3A:
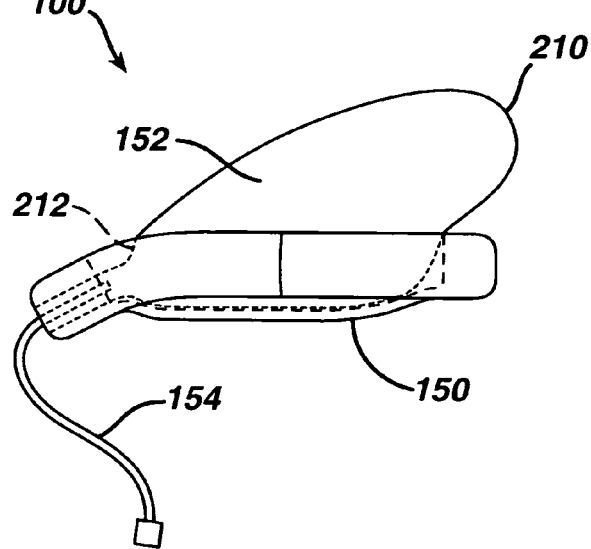
Figure 3B:
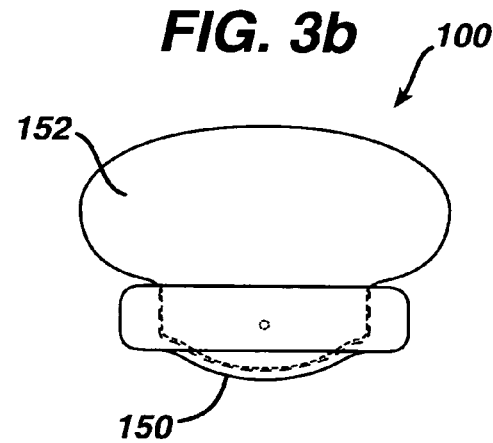

Referring now to FIG. 1, according to one embodiment, the intra-vaginal splint assembly 100 preferably comprises a single base portion 102 and two or more apical sections (i.e., 104a, 104b, 104c), any one of which can be coupled to the base portion as will be described further below. When any one apical section is coupled to the base portion, a splint 101 is formed that preferably has a substantially trapezoidal overall configuration (see FIG. 2) defined by first and second connecting portions 106, 108 (one of which is preferably longer than the other) and first and second side members 107, 109. The first and second side members 107, 109 consist of first and second sides 110, 112 that extend outwardly in a distal direction from first and second ends 114, 116 of the first connecting portion 106, and first and second sides 118, 120 that extend outwardly in a proximal direction from first and second ends 122, 124 of the second connecting portion 108 of the apical section 104a. These respective sides are coupled to one another, end to end, through at least first and second coupling elements 126, 128 at each side respectively. For each of the first and second coupling elements 126, 128, first 130, 132 and second 134, 136 ends thereof are received within corresponding cavities or recesses 138, 140; 142, 144 in the base portion and adjustable apical section respectively. The coupling elements and corresponding recesses may be of any suitable form and configuration so as to achieve a snug interference fit that will secure the two pieces together. Application of a predetermined force by a user, however, should preferably be able to overcome the interference fit to separate the two pieces. In the illustrated embodiment, the coupling elements are substantially rigid, rod-like elements having a bulbous-like portion 146 on their respective ends. The first ends 130, 132 may be permanently affixed to the base portion, with the second ends 134, 136 being removably receivable within the recesses 142, 144 of any of the apical sections. Alternatively, each apical section may have first and second coupling elements secured thereto, first ends of which are receivable within corresponding recesses in the base portion.

As indicated, the vaginal splint assembly includes two or more apical sections, and in the illustrated embodiment includes first 104a, second 104b and third 104c apical sections as shown in FIG. 1. Each apical section is similar in size and shape, but each has a different length $l_1$, $l_2$, $l_3$. Each further has similar recesses 142a, 142b; 144a, 144b having substantially similar sizes and shapes so as to receive therein the coupling elements as described above in conjunction with the first apical section 104a. With each apical section of the vaginal splint assembly having a different length, but otherwise similar configuration, the apical sections are interchangeable with the base portion, ensuring a splint 101 that better fits an individual patient.

The splint described above may be made out of medical grade silicone, polyurethane, polyvinylchloride (PVC), latex, or Santoprene™, although any other suitable biocompatible materials may be used, such as natural rubbers, and blends or combinations of the previously noted materials. The splint may be formed by liquid injection molding, thermoplastic molding, die cutting, machining, insert molding or any other manufacturing technique well known to those skilled in the art.

Preferably, the splint is resilient and at least partially bendable about its longitudinal axis X-X. This feature facilitates easy insertion of the splint into the vagina. The side members 107, 109 or portions thereof may also be reinforced to obtain a more rigid frame with rods, thicker walls, higher durometer plastic, contouring or shaping of the side arms to resist bending, or by selective heat treating of portions and the like.

The splint described above may also include a thin membrane 150 or the like extending across the top and/or bottom sides of the splint so as to substantially cover the area between the first and second connection portions 106, 108 and the first and second side members 107, 109. The splint preferably further includes an opening, hole or the like 160 that extends through the first connecting portion 106, through which an inflatable member 152, such as a balloon, can be passed and positioned within the space between the first and second connecting portions and the first and second side members, and the top and bottom membranes if present. The inflatable member may or may not be removably secured to the splint. Further details of such an inflatable member are shown in FIGS. 2-2b and 3-3b.

Attached to the inflatable member 152 is an inflating tube 154 having a lumen that communicates with the interior hollow of the inflatable member and through which fluid can be infused. The inflatable member is preferably positioned within the splint as described above in a deflated state as shown in FIGS. 2-2b. The combination splint and inflatable member is introduced into the vagina and pressurized by fluid infusion (e.g. with saline solution, air or the like) until it reaches a suitable inflated state such as that shown in FIGS. 3-3b. With the addition of the inflatable member, the splint can contact the lateral vaginal walls and superior aspect of the vagina, as well as the upper and lower walls of the vagina. Thus, the splint can more completely fill the hollow of the vagina into which it is inserted and contact a greater surface area relative to the prior art. Additionally, since the inflatable member is preferably connected to the splint loosely at only one end, pressure on the inflatable member is not directly translated to pressure on the splint. Consequently, the splint will remain in its desired position and not be subjected to torque forces produced by uneven contact between the balloon and vaginal walls. In this manner, the splint has a hemostatic effect thereby improving wound healing and strength, reduces movement and displacement of the mesh while it incorporates into the vaginal fascial tissues, and avoids the need to use supporting sutures in structures such as the sacrospinous ligament, the uterosacral ligaments or paravaginal tissues. Such sutures are often difficult to place and are associated with significant pain and patient morbidity.

The inflatable member preferably has a minimally extensible wall so that it expands to a large diameter under low pressure so as not to interfere with tissue perfusion. This provides equal pressure between the inflatable member and tissue at all contact points. To the contrary, an inflatable member having a higher inflation pressure and greatly extensible sidewalls is not easily conformable to a body cavity. Additionally, having a relatively thin wall provides good conformability of the inflatable member to the interior slope of the vagina without producing pressure points on the vaginal wall. Thus, the inflatable member conforms to the shape of the vagina instead of the vagina conforming to the shape of the inflatable member. Suitable materials for the inflatable member include polyurethane, polyester, polyethylene, silicones or other similar materials that can be formulated to have similar extension properties. Polyurethane, in particular, can be used to form such an inflatable member having ideal mechanical and geometrical properties, such as good tear, cutting and puncture resistance.

The inflatable member may be manufactured by any suitable method, such as blow molding, dip molding, extrusion molding, or injection molding. According to one preferred method, the inflatable member is blow molded on pre-extruded tubing, which is axially and radially stretched in a blow molding process where the polymeric chains are detangled and aligned in parallel.

Figure 5:
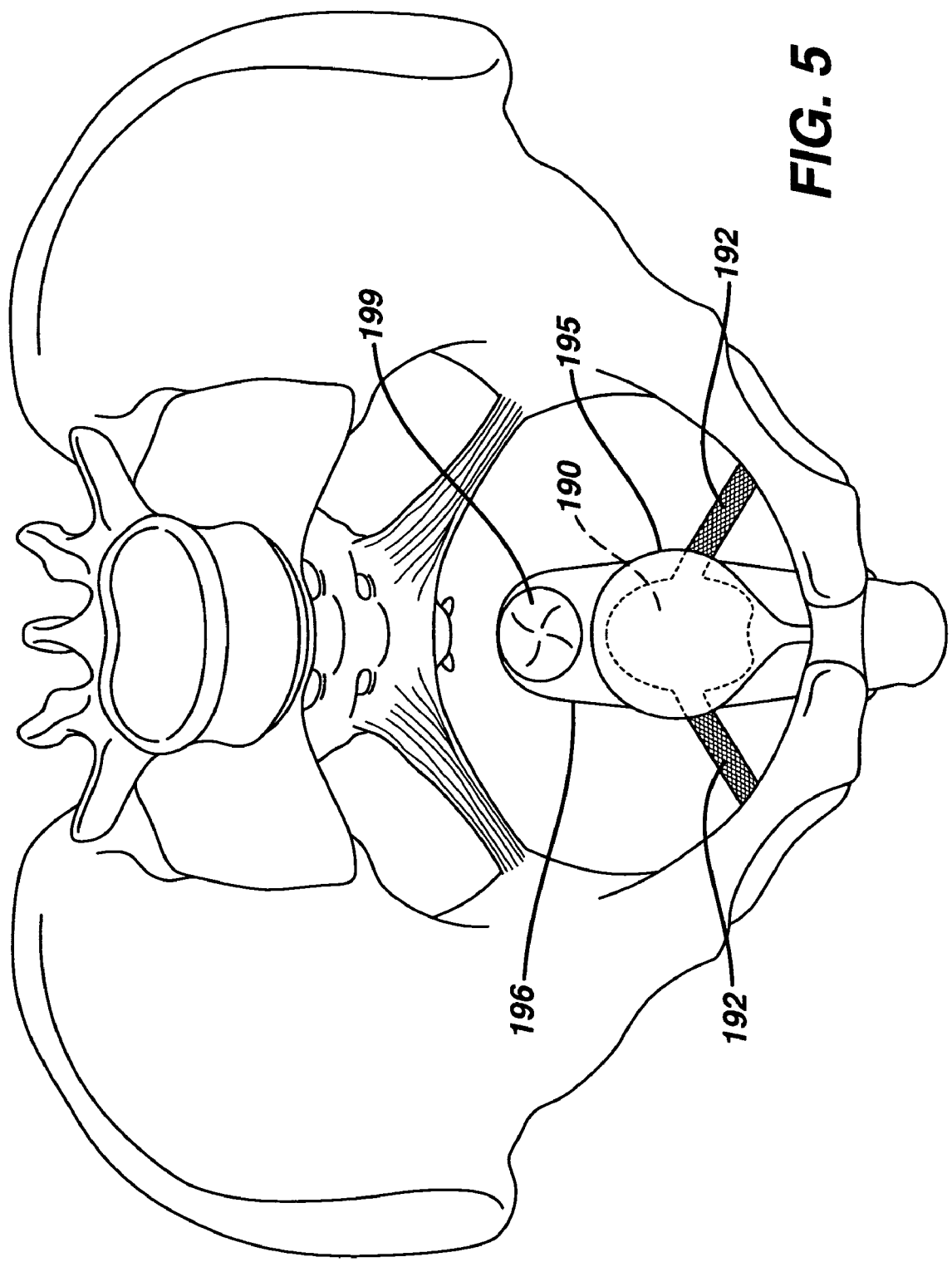
FIG. 5 illustrates placement of an exemplary mesh within the pelvis for treating a prolapse condition.

A method for treating a pelvic floor prolapse condition using a splint assembly according to the present invention will now be described with reference to FIGS. 4-7. For background reference, each of these FIGS. illustrates various aspects of the pelvic anatomy, including the bladder 195, vagina 196, cervix 199, and rectum 197. An incision is first made in the vaginal epithelium that covers the vaginal wall, and the epithelium peeled and held away from the fascia. Lateral dissection is then carried out to and through the arcus tendinous fascia pelvic on both sides, and into the paravaginal spaces. The fascia is preferably plicated once the epithelium has been mobilized off the fascia wall. A suitable implant, such as a mesh, is then positioned over the defect of the exposed fascia. One exemplary mesh for anterior repair is shown in FIG. 4. This mesh is made of polypropylene, and is manufactured and sold by Ethicon, Inc. of Somerville, N.J. The mesh 189 has a central body portion 190 that is substantially oval in shape, and has lateral extension arms 192. Once properly positioned over the defect, the lateral extension arms 192 of the mesh may be placed into the ipsilateral paravaginal space such that the lateral extension arms come into contact with the inner aspect of the pubic bone. The mesh may then be attached to the fascia by sutures to hold it in place during the remainder of the procedure. Excess vaginal epithelium is then trimmed and the anterior vaginal wall is closed by sutures. The position of the mesh within the pelvis is illustrated in FIG. 5.

Figure 6:
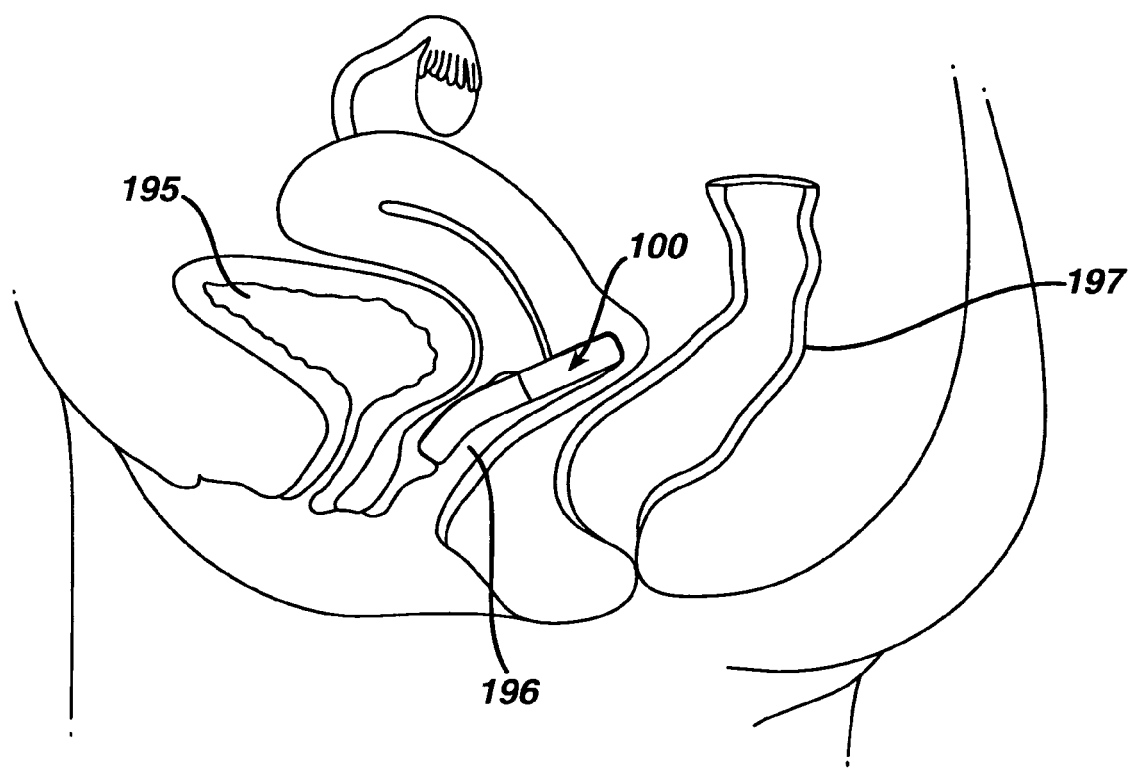
FIG. 6 is a side view illustrating placement of a splint of the present invention within a patient.
Figure 7:
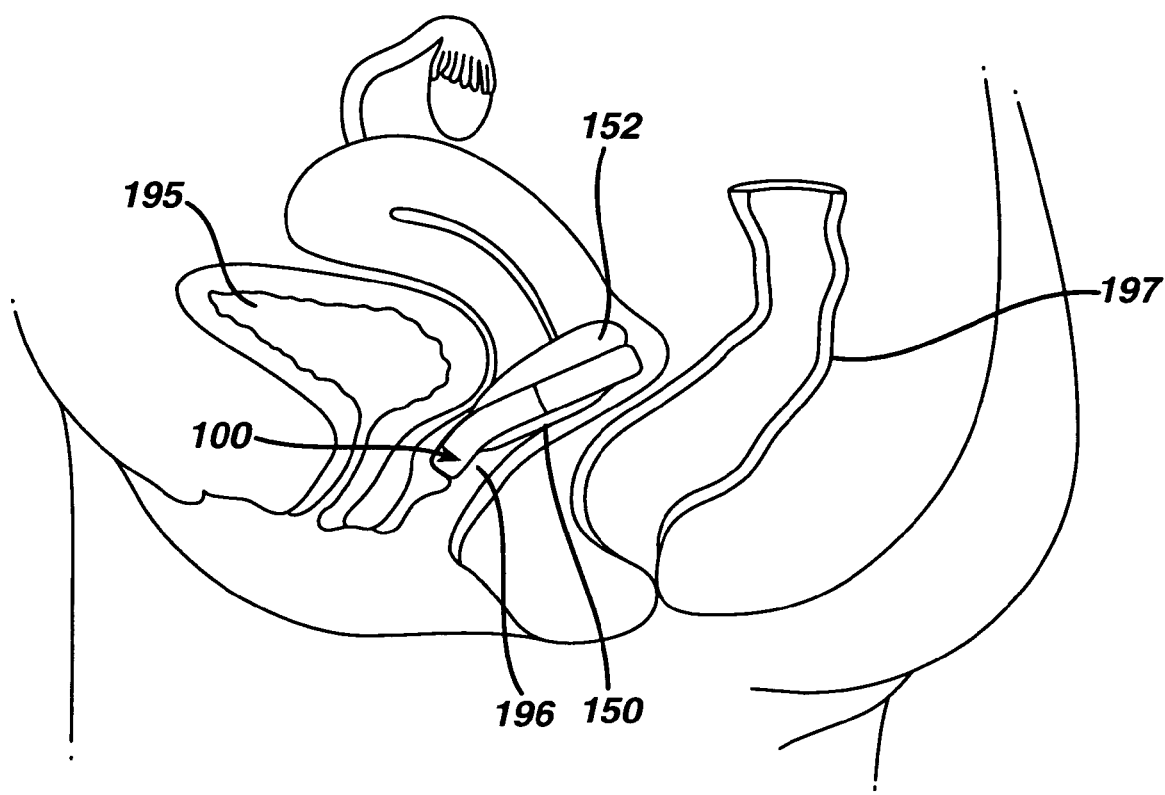
FIG. 7 illustrates the splint of FIG. 1 within a patient, with the inflatable member in an inflated state.

At this point the surgeon determines the size of the vagina. Once the correct size for the intra-vaginal splint has been determined and the appropriately sized apical section 104a, 104b, 104c is secured to the base portion as described above, the splint is inserted into the vagina as shown in FIG. 6. The splint may be secured within the vagina by one or more sutures or other attachment means to the epithelium of the vagina either in the anterior, posterior, or lateral walls. The inflatable member is then inflated as shown in FIG. 7 to help prevent the splint from dislodging from its desired position, or otherwise migrating during the healing period.

Referring back to FIG. 3, the inflatable member 152 is preferably shaped and sized so that it is larger in diameter at the distal end 210 than at the proximal end 212. This distal end is located in the apex of the vagina near the cervix, which is itself larger in diameter than the introital opening of the vagina and is more easily expandable. The inflatable member is preferably retained in the vagina for a period of 1-2 days, but may remain for a longer period if needed. The inflatable member can then be deflated and removed from the splint and the body. The intra-vaginal splint is preferably retained in the vagina for a period of four weeks, after which time the synthetic mesh has become incorporated into the tissue of each of the respective vaginal walls, and the splint can be removed.

As described above, the inflatable member acts as a tamponade as does the common practice of packing the vagina with gauze. The present device, however, provides several advantages in that it is more readily conformable to the vaginal cavity to provide better coverage for hemostasis, it is smoother and thus less painful, and it is adjustable. Further, as the splint does not absorb blood or other fluids, excessive or unusual bleeding can readily be detected.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. A vaginal splint kit comprising:
    a base portion having a connecting portion and first and second sides extending outwardly from first and seconds ends of the connecting portion to first and second free ends respectively;
    a plurality of apical sections each of a different size and each having a connecting portion and first and second sides extending outwardly from first and second ends of the connecting portion to first and second free ends respectively; and
    at least first and second coupling elements, the first coupling element capable of securing the first free end of the base portion to the first free end of any one of the plurality of apical sections such that the combination of the first side of the base portion and first side of the apical section are aligned free end to free end to form a substantially straight line, and the second coupling element capable of securing the second free end of the base portion to the second free end of said one apical section such that the combination of the second side of the base portion and the second side of the apical section are aligned free end to free end to form a substantially straight line,
    wherein a combination of the base portion and any one of the plurality of apical sections forms a vaginal splint adapted for placement within a vagina of a patient to thereby stabilize the vagina, and having a substantially trapezoidal shape defined by the first and second connecting portions and first and second sides of the base portion and the first and second sides of the apical section, said trapezoidal shape having a different size for each of the plurality of apical sections that is so coupled.

2. The assembly according to claim 1, wherein the first and second coupling elements are coupled to, and extend outwardly from the first and second free ends of the base portion to respective distal free ends.

3. The assembly according to claim 2, wherein the first and second free ends of each of the plurality of apical sections have first and second recesses therein configured to receive the respective distal free ends of the first and second coupling elements.

4. The assembly according to claim 3, wherein the distal ends of the first and second coupling elements form an interference fit with the respective first and second recesses.

5. The assembly according to claim 1, wherein each of the plurality of apical sections have first and second coupling elements coupled to and extending outwardly from the first and second free ends thereof respectively.

6. The assembly according to claim 5, wherein the first and second free ends of the base portion have first and second recesses therein configured to receive the distal free ends of the first and second coupling elements of any one of the plurality of apical sections.

7. A vaginal splint kit comprising:
    a base portion having a connecting portion and first and second sides extending outwardly from first and seconds ends of the connecting portion to first and second free ends respectively;
    a plurality of apical sections each of a different size and each having a connecting portion and first and second sides extending outwardly from first and second ends of the connecting portion to first and second free ends respectively;
    at least first and second coupling elements, the first coupling element capable of securing the first free end of the base portion to the first free end of any one of the plurality of apical sections, and the second coupling element capable of securing the second free end of the base portion to the second free end of said one apical section; and
    an inflatable member positioned between the first and second sides of the base portion, the inflatable member being inflatable by infusion of fluid or gas therein, and, when in the inflated state, the inflatable member extends outwardly beyond a top and/or bottom surface of the splint.

8. The assembly according to claim 7, wherein the inflatable member is a balloon comprised of a material selected from the group consisting of polyurethane, polyester, silicone and rubber.

9. The assembly according to claim 7, wherein the inflatable member is detachably coupled to the splint assembly.

10. A method for treating a pelvic floor prolapse condition of a patient comprising:
    providing a vaginal splint kit including base portion having a connecting portion and first and second sides extending outwardly from first and seconds ends of the connecting portion to first and second free ends respectively, a plurality of apical sections each of a different size and each having a connecting portion and first and second sides extending outwardly from first and second ends of the connecting portion to first and second free ends respectively, and at least first and second coupling elements, wherein the first coupling element is capable of securing the first free end of the base portion to the first free end of any one of the plurality of apical sections, and the second coupling element is capable of securing the second free end of the base portion to the second free end of said one apical section;

determining a size of the patient's vagina;

based on the determined size, selecting one of the plurality of apical sections;

coupling the selected apical section to the base portion via the at least first and second coupling elements to form a vaginal splint; and inserting the vaginal splint into the patient's vagina.

11. The method according to claim 10, wherein when any one of the plurality of adjustable apical sections is secured to the base portion, the splint has a substantially trapezoidal overall configuration.

12. The method according to claim 10, wherein the first and second coupling elements are secured to the base portion, and configured such that any one of the plurality of apical sections may be coupled to the base portion via the coupling elements.

13. The method according to claim 12, wherein the first and second coupling elements extend outwardly from the first and second free ends of the base portion to respective distal ends, and wherein the first and second free ends of each of the plurality of apical sections have respective first and second recesses therein configured to removably receive therein the respective distal free ends of the first and second coupling elements.

14. The method according to claim 13, wherein the distal ends of the first and second coupling elements form an interference fit with the respective first and second recesses.

15. The method according to claim 10, wherein the splint assembly further comprises an inflatable member positioned between the first and second sides of the base portion, the method further comprising, following the inserting step, inflating the inflatable member by infusing fluid or gas therein until the inflatable member extends outwardly beyond a top and/or bottom surface of the splint.

16. The method according to claim 15, wherein the inflatable member is a balloon comprised of a material selected from the group consisting of polyurethane, polyester, silicone and rubber.

17. The method according to claim 16, further comprising the step of removing the vaginal splint from the patient after a first time period has elapsed.

18. The method according to claim 17, wherein the inflatable member is detachably coupled to the splint, and wherein the removing step further comprises deflating and removing the inflatable member after a first time period has elapsed, and removing the splint after a second time period has elapsed that is greater than the first time period.

* * * * *